United States Patent [19]

Rössling et al.

[11] Patent Number: 5,593,687
[45] Date of Patent: Jan. 14, 1997

[54] AQUEOUS DISPERSION CONTAINING LIPOSOMES

[75] Inventors: Georg Rössling; Andreas Sachse, both of Berlin, Germany

[73] Assignee: Schering Aktiengesellschaft, Germany

[21] Appl. No.: 815,224

[22] Filed: Dec. 31, 1991

Related U.S. Application Data

[62] Division of Ser. No. 596,920, Oct. 15, 1990, Pat. No. 5,110,475.

[30] Foreign Application Priority Data

Oct. 13, 1989 [DE] Germany .......................... 39 34 656.0

[51] Int. Cl.$^6$ .................................................. A61K 9/127
[52] U.S. Cl. ........................ 424/450; 210/640; 210/651
[58] Field of Search ............................ 424/450, 4, 5; 210/640, 651

[56] References Cited

U.S. PATENT DOCUMENTS

| | | | |
|---|---|---|---|
| 2,386,826 | 10/1945 | Wallach | 210/85 |
| 3,035,060 | 5/1962 | Binning | 260/290 |
| 4,199,445 | 4/1980 | Chiang | 210/640 |
| 4,670,146 | 6/1987 | Inoue | 210/490 |
| 4,728,429 | 3/1988 | Cabasso | 210/638 |
| 4,744,989 | 5/1988 | Payne | 424/5 |
| 4,798,674 | 1/1989 | Pasternak | 210/640 |
| 4,877,529 | 10/1989 | Pasternak | 210/500.37 |
| 4,935,144 | 6/1990 | Pasternak | 210/640 |
| 4,957,729 | 9/1990 | Counsell | 424/5 |

FOREIGN PATENT DOCUMENTS

| | | |
|---|---|---|
| 2935195 | 4/1980 | Germany . |
| 2157283 | 10/1985 | United Kingdom . |

OTHER PUBLICATIONS

Sovak in Radio contrast agents p. 1, 1984.

*Primary Examiner*—Gollamudi S. Kishore
*Attorney, Agent, or Firm*—Millen, White, Zelano, & Branigan, P.C.

[57] ABSTRACT

A process is described for the production of aqueous dispersions involving removal of liquid(s) from an optionally multiphase liquid mixture by means of membrane distillation, e.g., transmembrane distillation or pervaporation.

11 Claims, No Drawings

AQUEOUS DISPERSION CONTAINING LIPOSOMES

This is a division, of application Ser. No. 07/596,920 filed Oct. 15, 1990 now U.S. Pat. No. 5,110,475.

SUMMARY OF THE INVENTION

The invention relates to a process for the preparation of aqueous dispersions, characterized by removing liquid(s) from an optionally multiphase liquid mixture by means of membrane distillation (e.g., transmembrane distillation or pervaporation).

The process of this invention is suitable for the production of dispersions such as, for example, aqueous suspensions, aqueous emulsions, e.g., o/w emulsions and o/w/o emulsions, and aqueous formulations containing liposomes, micelles, colloids, etc.

The liquid mixtures are optionally multiphase. For example, the mixture can contain multiple liquid phases or both solid and liquid phases.

Liquids that can be separated by means of the process of this invention are preferably those having a boiling point of maximally about 300° C. Such liquids are, for example, water, alcohols, such as methanol, ethanol, propanol or isopropanol, ketones, such as acetone, esters, such as ethyl acetate, ethers, such as diethyl ether, diisopropyl ether, dioxane or tetrahydrofuran, halogenated hydrocarbons, such as dichloromethane, trichlorofluoromethane, hydrocarbons, such as pentane, hexane, heptane, octane, neopentane, isopentane, cyclopentane, or polar aprotic solvents, such as acetonitrile, dimethyl sulfoxide or dimethylformamide.

The process of this invention is, of course, also suited for separating mixtures of the aforementioned liquids. The process according to the invention is preferably performed by removing the liquids by means of transmembrane distillation or pervaporation.

As is known, aqueous suspensions of organic compounds are frequently prepared by dissolving the compound to be suspended in an organic solvent, then adding an aqueous phase dropwise to the resultant solution under vigorous turbulence, and removing the solvent by vacuum distillation.

A basically similar procedure could also be followed in the production of colloids or emulsions. However, this method seems to be less popular since there is the risk of coagulation of the colloids and emulsions during removal of the solvents by distillation.

Aqueous phases containing liposomes or micelles are frequently produced by dissolving the liposome- or micelle-forming compounds and, if desired, also the active ingredients (e.g., medicinal agents) in a solvent, introducing the solution into the aqueous phase, the latter also optionally containing active ingredients, and, if desired after homogenization, removing the solvent by distillation ("Pharmazie in unserer Zeit" [Pharmacy in Our times] 11: 97–108, 1982; Pure and Appl. Chem. 53: 2241–2254, 1981; DE-A 2,730, 570).

Surprisingly, if, in the preparation of such dispersions, the liquid to be removed is removed by membrane distillation, rather than by simple distillation, the particle sizes of the resultant dispersion can be freely selected within wide limits. Also, the dispersions exhibit a significantly more uniform particle distribution. Moreover, the process of this invention has the advantage, especially when preparing phase mixtures containing liposomes or micelles, that it can be performed on an industrial scale substantially more simply than, for example, the REV process (see U.S. Pat. No. 4,235,871). As is known, the REV process is of little suitability for industrial production of such dispersions.

Generally, the process can be used to prepare dispersions wherein the particle size is about 1–100,000 nm. For micelle formulations, liposome formulations, emulsions, and suspensions the particle sizes are, for example, about 3–20 nm, about 30–3000 nm, about 100–10,000 nm, and 100–100,000 nm, respectively.

The term membrane distillation is understood to mean, according to this invention, particularly the conventional methods of transmembrane distillation (Chem. Ing. Techn. 56: 514–521, 1984; J. of Membrane Sci. 39: 25–42, 1988; DE-A 3,312,359) and of pervaporation (Swiss Chem. 10: 45–51, 1988; ACS Symposium 281: 467–478, 1985; Chem. Ing. Tech. 60: 590–603, 1988).

In transmembrane distillation (TMD) which has been utilized in the purification of water and in the grocery industry, the liquid to be removed is discharged, as is known, via a hydrophobic, symmetrical microporous membrane. Suitable membranes are, for example, those of polyolefins, such as polypropylene and polyfluorinated hydrocarbons, such as polytetrafluoroethylene and polyvinylidene fluoride, having a pore size of about 0.1–0.5 μm, molded into capillaries of a diameter of about 1–2 mm and a wall thickness of about 0.5–1 mm. Transmembrane distillation is usually conducted with filtration modules containing the corresponding membrane in tubular or capillary form. In order to obtain adequate permeative flow, the temperature difference between the aqueous dispersion present in the interior of the capillaries and the permeative substance present outside the capillaries should be set to a range of about 1°–100° C., preferably 10°–60° C. Furthermore, the application of a pressure gradient is suitable for obtaining adequate membrane flow. The size of the pressure depends on the compressive strength of the membrane utilized and is normally maximally about $10^6$ Pa, preferably up to about 30,000 Pa.

Transmembrane distillation is suitable for removing volatile organic solvents having a higher vapor pressure than water from the liquid mixtures, as well as for concentrating the thus-obtained dispersions. Generally, the vapor pressure difference between water and the organic solvent to be removed is about 1000–10,000 Pa. Preferably, a vacuum is present outside the membrane.

In pervaporation, already utilized industrially for the removal of ethanol from fermentation broths, the liquid to be removed is, as is known, discharged via an asymmetrical membrane devoid of pores. Flow of a material through the membranes is related to its solubility within the membrane material. Suitable membranes are, for example, those of polydimethylsiloxane or poly-vinyl alcohol having a thickness of about 0.1–2 μm, applied to a spongy or tissue-like supporting layer. Suitable membrane modules are also capillary and tubular modules or also plate modules or spirally wound modules. As for the development of solvent-selective membranes and their mode of operation, attention is invited to the aforementioned publication in the periodical Chem. Ing. Techn. 60: 590 et seq., 1988.

The pervaporation method can be used not only for removing solvents from aqueous dispersions wherein the solvents have a higher vapor pressure than water, but also can be used for removal of solvents having a vapor pressure lower than that of water, such as, for example, dimethylformamide, dimethyl sulfoxide or acetonitrile.

As mentioned above, the process according to the invention is suited for the preparation of aqueous suspensions of active compounds which show poor solubility or insolubility in water, for example, their solubility in water at room temperature not exceeding about 2%. Such active ingredients include plant protective agents, such as sparingly soluble insecticides or herbicides and, in particular, sparingly soluble pharmaceutically active agents.

For example, sparingly water-soluble or water-insoluble pharmaceutically active compounds which are members of the following active agent groups can be used for the preparation of aqueous suspensions according to the process of this invention:

Gestagenically active steroid hormones, such as, for example, 13-ethyl-17β-hydroxy-18,19-dinor-17α-pregn-4-en-20-yl-3-one (=levonorgestrel); 13-ethyl-17β-hydroxy-18,19-dinor-17α-pregna-4,15-dien-20-yn-3-one (=gestodene); or 13-ethyl-17β-hydroxy-11-methylene-18,19-dinor-17α-pregn-4-en-20-yne (=desogestrel), estrogenically active steroid hormones, such as 3-hydroxy-1,3,5(10)-estratrien-17-one (=estrone) or 1,9-nor-17α-pregna-1,3,5(10)-trien-20-yne-3,17β-diol (=ethynylestradiol).

Androgenically active steroid hormones, such as 17β-hydroxy-4-androsten-3-one (=testosterone) and its esters, or 17β-hydroxy-1α-methyl-5α-androsten-3-one (=mesterolone).

Antiandrogenically effective steroid hormones, such as 17α-acetoxy-6-chloro-1β,2β-dihydro-3'H-cyclopropa[1,2]pregna-1,4,6-triene-3,20-dione (=cyproterone acetate).

Corticoids, such as 11β,17α,21-trihydroxy-4-pregnene-3,20-dione (=hydrocortisone), 11β,17α,21-trihydroxy-1,4-pregnadiene-3,20-dione (=prednisolone), 11β,17α,21-trihydroxy-6α-methyl-1,4-pregnadiene-3,20-dione (=methylprednisolone), and 6α-fluoro- β,21-dihydroxy-16α-methyl-1,4-pregnadiene-3,20-dione, (=diflucortolone) and their esters.

Ergolines, such as 3-(9,10-dihydro-6-methyl-8α-ergolinyl)-1,1-diethylurea (=ergoline), 3-(2-bromo-9,10-dihydro-6-methyl-8α-ergolinyl)-1,1-diethylurea (=bromoergoline) or 3-(6-methyl-8α-ergolinyl)-1,1-diethylurea (=terguride).

Antihypertensives, such as 7α-acetylthio-17α-hydroxy-3-oxo-4-pregnene-21-carboxylic acid-δ-lactone (=spironolactone) or 7α-acetylthio-15β,16β-methylene-3-oxo-17α-pregna-1,4-diene-21,17-carbolactone (=mespirenone).

Anticoagulants, such as 5-[hexahydro-5-hydroxy-4-(3-hydroxy-4-methyl-1-octen-6-ynyl)-2(1H)-pentalenylidene] pentanoic acid (=iloprost).

Psychopharmaceuticals, such as 4-(3-cyclopentyloxy-4-methoxyphenyl)-2-pyrrolidone (=rolipram) and 7-chloro-1,3-dihydro-1-methyl-5-phenyl-2H-1,4-benzodiazepin-2-one (=diazepam).

Cartenoids, such as α-carotene and β-carotene.

Fat-soluble vitamins, such as vitamins of the vitamin A, vitamin D, vitamin E and vitamin K groups.

A further group is represented by the β-carbolines, as they are disclosed, for example, in European Patent Applications 234,173 and 239,667. Examples of β-carbolines are the isopropyl ester of 6-benzoyloxy-4-methoxymethyl-β-carboline-3-carboxylic acid (=becarnil) and the isopropyl ester of 5-(4-chlorophenoxy)-4-methoxymethyl-β-carboline-3-carboxylic acid (=Cl-PHOCIP).

Also worth mentioning are sparingly soluble contrast media, such as the radiopaque agent iodipamide ethyl ester, or NMR contrast media, such as the iron or manganese porphyrin chelates.

The aqueous suspensions produced in accordance with the process of this invention can optionally contain the customary dispersants, such as, for example, polyvinylpyrrolidone, lecithins or Pluronics®, preservatives, and furthermore isotonic additives to increase osmotic pressure to 5–1,000 mosm. The aqueous suspensions can be utilized, for example, as injection suspensions.

The process according to this invention is likewise suitable, in the same way as described above, for the removal of liquids from colloidal suspensions and emulsions. The process can be used, for example, in the preparation of gels, ointments or lotions which optionally contain active ingredients. Active compounds suited for the production of such galenic formulations are, for example, the aforementioned corticoids and antiandrogenically effective materials.

The process of this invention offers special advantages in the manufacture, on an industrial scale, of phase mixtures which contain liposomes or micelles since these mixtures, as mentioned above, can be manufactured in relatively large quantities only with difficulty by means of the previously known methods.

Phase mixtures containing liposomes or micelles are, as is known, of significance, inter alia, for the encapsulation or solubilizing of active compounds. According to the invention, they are prepared by dissolving the compounds forming liposomes and/or micelles, and optionally also the active ingredient(s), in a volatile organic solvent (e.g., ethanol, ethyl acetate, diethyl ether), introducing the solution into the aqueous phase, the latter also optionally containing the active compound(s), if desired, and removing the solvent by transmembrane distillation or pervaporation.

Suitable compounds which form micelles are, in particular, salts of bile acids utilized in combination with lipids for the production of aqueous mixed micelle solutions (DE-A 2,730,570).

Examples of suitable bile acids are: cholic acid, glycocholic acid, taurocholic acid, deoxycholic acid, glycodeoxycholic acid, taurodeoxycholic acid, chenodeoxycholic acid, glycochenodeoxychloic acid, and taurochenodeoxycholic acid.

In order to prepare the aqueous mixed micelle solutions, the process of this invention can employ the same lipids as used in the conventional methods.

Suitable lipids include, for example, monoglycerides, sulfatides and, in particular, phospholipids, such as the sphingomyelins, the plasmalogens, the phosphatidylcholines, the phosphatidylethanolamines, the phosphatidylserines, the phosphatidylinositols, and the cardiolipins, as well as mixtures of these lipids (Dr. Otto-Albert Neumüller: Römpps Chemie-Lexikon; Franckh'sche Verlagshandlung, Stuttgart [Germany] 2665; 3159; 3920; and 4045).

For preparing the aqueous mixed micelle solutions, preferably about 3–40%, and especially about 5–20% lipid per 100 g of the aqueous solution is used and the aqueous solution optionally contains isotonizing additives and/or water-soluble active compounds. The weight ratio between lipid and bile acid is preferably about 0.1:1 to 2:1, especially about 0.8:1 to 2:1.

Suitable bases for preparing the salts of the bile acids include, for example, alkali hydroxides, such as lithium hydroxide, potassium hydroxide and especially also sodium hydroxide.

The aqueous mixed micelle solutions prepared according to the process of this invention can contain isotonic additives, if desired, in order to increase the osmotic pressure.

Suitable additives include, for example, inorganic or organic salts or buffers, such as sodium chloride, phosphate buffer, citrate buffer, glycine buffer, citrate-phosphate buffer, maleate buffer, etc., mono- or disaccharides, such as glucose, lactose, sucrose, sugar alcohols, such as mannitol, sorbitol, xylitol or glycerol, or water-soluble polymers, such as dextran or polyethylene glycol.

These isotonizing compounds are customarily added in such concentrations that the resultant aqueous mixed micelle solution exhibits an osmotic pressure of about 5–1,000 mosm—in the case of injection solutions optimally about 300 mosm.

Except, of course, for the above-described membrane distillation procedure, the water-soluble mixed micelle solutions according to the invention are prepared in accordance with conventional methods.

Since the lipids and also several active compounds are sensitive to oxidation, the process is suitably conducted under an inert gas atmosphere, such as nitrogen or argon, and the thus-obtained aqueous mixed micelle solutions are stabilized by the addition of antioxidants, such as sodium ascorbate, tocopherol, or sodium hydrogen sulfite.

These mixed micelle solutions can be utilized, for example, for solubilizing the aforementioned sparingly soluble active compounds.

The aqueous mixed micelle solutions can furthermore contain additional water-soluble active ingredients in order to produce combination preparations. Examples of such combination preparations are mixtures of water-soluble and fat-soluble vitamins, or preparations containing also water-soluble antibiotics besides corticoids.

For preparing liposome-containing, aqueous phase mixtures, the aforementioned phospholipids and mixtures of these phospholipids with cholesterol and/or charge carriers, e.g., stearylamine, stearic acid or diacetyl phosphate are preferably utilized. In this case, preferably about 0.1–40% by weight and especially about 1–20% by weight of phospholipid or mixture is employed, based on the aqueous phase. Suitable mixtures contain approximately up to about 60% by weight of cholesterol and up to about 15% by weight of charge carrier. Solvents used for the phospholipids or mixtures are preferably methanol, ethanol, isopropanol, diethyl ether, dioxane, acetone, chloroform, acetonitrile, dimethyl sulfoxide and mixtures of these solvents.

The process according to the invention is performed, apart from the membrane distillation procedure, under the same conditions as the previously known methods (Pharmazie in unserer Zeit 11: 97–108, 1982; Pure Appl. Chem. 53: 2241–2254, 1981). The process is suitable for preparing multilamellar liposomes as well as also for producing unilamellar liposomes and is particularly suited for the manufacture of large unilamellar liposomes by means of reverse phase evaporation.

The liposome-containing, aqueous phase mixtures can contain the same additives as the mixed micelle solutions and can serve, for example, for encapsulating water-soluble active materials.

Such water-soluble active materials are, for example, diagnostic media, such as the X-ray contrast media iotrolan, iohexol, iosimide, metrizamide, salts of amidoacetic acid, and especially iopromide, or NMR contrast media, such as gadolinium DTPA.

Suitable medically active compounds are, inter alia, antibiotics, such as gentamycin or kanamycin, cytostatics, such as doxorubicin hydrochloride or cyclophosphamide, and antiviral agents, such as vidarabine.

Moreover, the liposome-containing, aqueous phases can also be utilized for encapsulation of the aforementioned active ingredients which show poor solubility in water.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany DE 39 34 656.0, filed Oct. 13, 1989, are hereby incorporated by reference.

EXAMPLES

Example 1

12 g of phosphatidylcholine is dissolved in 500 ml of diethyl ether, and this solution is transferred into a flask charged with 500 ml of an active compound solution containing 400 mg of iotrolan per milliliter. This mixture is homogenized by means of a high-pressure homogenizer, thus forming a kind of water-in-oil emulsion wherein the aqueous phase present is dispersed in the form of "inverse micelles". This emulsion is subsequently conveyed by means of a gear pump in circulating mode through two series-connected filtration modules made up of respectively three polypropylene tube members (Labormodul® by Enka AG, De-5600 Wuppertal). The fluid is circulated from a storage vessel through the two series-connected filtration modules and then back to the storage vessel (i.e., cyclic mode).

A pressure of 8,000 Pa is applied during this procedure to the outside of the membrane by means of an evacuating unit. Thus, a vacuum is present at the exterior of the membrane. During removal of the solvent, the storage vessel, exhibiting a temperature-controllable jacket, is maintained at temperatures of between 30° and 35° C.

The initial throughflow rate is 6 l/min, and the module inlet pressure resulting therefrom is 70,000 Pa. These two parameters are observed by means of a manometer and a flowmeter during solvent removal. After a time as short as 15 minutes, initial gel structures have been formed which are stripped off the walls of the storage vessel repeatedly during separation. The throughflow rate decreases during the course of continued separation; a rise in module inlet pressure is recorded. After 50 minutes, a viscous gel is formed whereby the module inlet pressure of 150,000 Pa, maximally permissible according to the manufacturer's specifications, is exceeded. The ether content at this point is 5–10%. Addition of 150 ml of buffer solution (0.015M Tris-HCl buffer, pH 7.4) in incremental portions has the result of inducing breakup of the gel and formation of an aqueous liposome suspension. By continued membrane distillation in the cycle, the ether concentration can be lowered to below 2%.

Example 2

12 g of phosphatidylcholine is dissolved in 125 ml of ethanol, and this solution is transferred into a flask charged with 500 ml of an aqueous active compound solution containing 400 mg of iotrolan per milliliter. The mixture is subsequently mixed by shaking.

This mixture is then conveyed by means of a gear pump in circulation mode through two series-connected filtration modules made up of respectively three polypropylene tube membranes (Labormodul® by Enka AG, DE-5600 Wuppertal).

During this step, 1,000 ml of distilled water, cooled by means of a methanol dry ice mixture (5°–10° C.) is passed countercurrently over the outside of the membrane. During removal of the solvent, the storage vessel, exhibiting a temperature-controllable jacket, is maintained at temperatures around 35° C.

The initial flow rate is 5 l/min, and the resultant module inlet pressure is 50,000 Pa. These two parameters are observed during solvent removal by means of a manometer and a flowmeter. After about 2 hours, a whitish liposome suspension is obtained. The average diameter of the liposomes contained therein is 261.7±5 nm. The iotrolan occluded therein is 25 mg of iotrolan/ml, and the residual ethanol content is below 1%.

Example 3

32.4 g of a mixture of phosphatidylcholine, cholesterol and stearic acid (4:5:1) is dissolved at an elevated temperature in 350 ml of ethanol. This solution is transferred under agitation into a flask containing 700 ml of an aqueous solution of 32.5 g of iopromide in 0.020 Tris-HCl buffer (pH 7.5). Separation of the ethanol is then performed as described in Example 2. In a deviation from the aforementioned example, the storage vessel is, however, temperature-controlled to be at 55° C.

After about 5 hours, whitish liposome suspensions are also obtained in this case. The average diameter of the liposomes contained therein is 370 nm, and the iopromide occlusion is 36%, based on the total contrast medium concentration. The residual ethanol content is less than 0.1%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aqueous dispersion comprising an aqueous dispersion medium, liposomes, and iopromide encapsulated in said liposomes, wherein said dispersion is prepared by removing an organic solvent from a liquid mixture of an aqueous phase and an organic solvent, said solvent having liposome-forming compounds contained therein, by means of membrane distillation.

2. An aqueous dispersion according to claim 1, wherein said dispersion further contains inorganic or organic salts or buffers, monosaccharides, disaccharides, sugar alcohols, or water-soluble polymers.

3. An aqueous dispersion according to claim 2, wherein said dispersion further contains sodium chloride, phosphate buffer, citrate buffer, glycine buffer, citrate-phosphate buffer, maleate buffer, glucose, lactose, sucrose, mannitol, sorbitol, xylitol, glycerol, dextran, or polyethylene glycol.

4. An aqueous dispersion according to claim 1, wherein said dispersion further contains an anti-oxidant.

5. An aqueous dispersion according to claim 4, wherein said anti-oxidant is sodium ascorbate, tocopherol, or sodium hydrogen sulfite.

6. An aqueous dispersion according to claim 1, wherein said dispersion further contains a sphingomyelin, a plasmalogen, a phosphatidylcholine, a phosphatidylethanolamine, a phosphatidylserine, a phosphatidylinositol, or a cardiolipin.

7. An aqueous dispersion according to claim 6, wherein said dispersion further contains cholesterol.

8. An aqueous dispersion according to claim 6, wherein said dispersion further contains a charge carrier selected from the group consisting of stearylamine, stearic acid, or diacetylphosphate.

9. An aqueous dispersion according to claim 6, wherein said dispersion contains 0.1–40 wt % phospholipid or phospholipid mixture based on the total aqueous phase.

10. An aqueous dispersion according to claim 7, wherein said dispersion contains up to 60 wt. % cholesterol.

11. An aqueous dispersion according to claim 8, wherein said dispersion contains up to 15 wt % of said charge carrier.

* * * * *